US012760327B2

(12) United States Patent
Yobas et al.

(10) Patent No.: US 12,760,327 B2
(45) Date of Patent: Oct. 13, 2026

(54) DEVICE FOR CELL TREATMENT

(71) Applicant: THE HONG KONG UNIVERSITY OF SCIENCE AND TECHNOLOGY, Hong Kong (CN)

(72) Inventors: Levent Yobas, Hong Kong (CN); Yang Bu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 798 days.

(21) Appl. No.: 18/159,721

(22) Filed: Jan. 26, 2023

(65) Prior Publication Data

US 2023/0279437 A1 Sep. 7, 2023

Related U.S. Application Data

(60) Provisional application No. 63/303,463, filed on Jan. 26, 2022.

(51) Int. Cl.
*C12N 15/87* (2006.01)
*B01L 3/00* (2006.01)
(Continued)

(52) U.S. Cl.
CPC ........ *C12N 15/87* (2013.01); *B01L 3/502761* (2013.01); *C12M 23/16* (2013.01);
(Continued)

(58) Field of Classification Search
CPC ............... C12N 15/87; B01L 3/502761; B01L 2200/0652; B01L 2300/0645;
(Continued)

(56) References Cited

U.S. PATENT DOCUMENTS

| | | | |
|---|---|---|---|
| 6,749,736 | B1 | 6/2004 | Fuhr et al. |
| 11,377,652 | B2 | 7/2022 | Chang |

(Continued)

FOREIGN PATENT DOCUMENTS

| | | | |
|---|---|---|---|
| WO | 2019/161165 | A1 | 8/2019 |

OTHER PUBLICATIONS

Xing, X et al, Dielectrophoretic isolation of cells using 3D microelectrodes featuring castellated blocks, Analyst, 2015, 140, 3397-3405. (Year: 2015).*

(Continued)

*Primary Examiner* — Christine T Mui
(74) *Attorney, Agent, or Firm* — SALIWANCHIK, LLOYD & EISENSCHENK

(57) ABSTRACT

A flow-through microfluidic apparatus for cell treatment is provided, including a flow chamber and a three-dimensional (3D) microelectrode array disposed in the flow chamber to produce electrical fields for cell railing, electroporation and/or sorting. The flow chamber includes a sample flow region, a first sheath flow region and a second sheath flow region. The sample flow region has an input allowing a sample flow of cells and exogenous agents to enter the sample flow region, a first output allowing damaged cells to exit from the flow chamber. Viable target cells are dielectrophoretic railed along the plurality of 3D microelectrode units; railing cells are electroporated through electrical treatment to intake/uptake of an exogenous agent; and viable treated cells loaded with exogenous agent are dielectrophoretically sorted from cells damaged during the cell treatment.

16 Claims, 13 Drawing Sheets

(51) Int. Cl.
*C12M 1/00* (2006.01)
*C12M 1/42* (2006.01)
*C12M 3/06* (2006.01)

(52) U.S. Cl.
CPC ............ *C12M 29/04* (2013.01); *C12M 35/02* (2013.01); *B01L 2200/0652* (2013.01); *B01L 2300/0645* (2013.01)

(58) Field of Classification Search
CPC ....... B01L 3/502776; B01L 2200/0636; B01L 2300/0816; B01L 3/502753; B01L 2400/0424; B01L 2400/086; C12M 23/16; C12M 29/04; C12M 35/02
USPC .................................................. 422/502, 500
See application file for complete search history.

(56) References Cited

U.S. PATENT DOCUMENTS

| | | | |
|---|---|---|---|
| 2009/0155877 | A1 | 6/2009 | Iliescu et al. |
| 2020/0071727 | A1 | 3/2020 | Tandon et al. |
| 2020/0115668 | A1 | 4/2020 | Borenstein et al. |
| 2020/0399578 | A1 | 12/2020 | Corso et al. |
| 2021/0370292 | A1 | 12/2021 | Douglas et al. |
| 2023/0132556 | A1 | 5/2023 | Shkolnikov et al. |

OTHER PUBLICATIONS

Tang, Multifunctional 3D Viaduct Microelectrodes for Continuous-Flow Dielectrophoretic Railing and Electroporation of Cells Under Modulated Activation, Transducers 2021 Virtual Conference Jun. 20-24, 2021. (Year: 2021).*

Wei, Z., et al., "Flow-Through Cell Electroporation Microchip Integrating Dielectrophoretic Viable Cell Sorting," Analytical Chemistry, 2014, 86:10215-10222.

Selmeczi, D., et al., "Efficient large volume electroporation of dendritic cells through micrometer scale manipulation of flow in a disposable polymer chip," Biomed Microdevices, 2011, 13:383-392.

Kim, S.K., et al., "Continuous Low-Voltage dc Electroporation on a Microfluidic Chip with Polyelectrolytic Salt Bridges," Analytical Chemistry, 2007, 79(20):7761-7766.

Lissandrello, C.A., et al., "High-throughput continuous-flow microfluidic electroporation of mRNA into primary human T cells for applications in cellular therapy manufacturing," Scientific Reports, 2020, 10:1-16.

Bhattacharjee, N., et al., "Continuous-flow multi-pulse electroporation at low DC voltages by microfluidic flipping of the voltage space topology," Applied Physics Letters, 2016, 109:1-6.

Geng, T., et al., "Flow-through electroporation based on constant voltage for large-volume transfection of cells," Journal of Controlled Release, 2010, 144:91-100.

Punjiya, M., et al., "A flow through device for simultaneous dielectrophoretic cell trapping and AC electroporation," Scientific Reports, 2019, 9:1-11.

Xing, X., et al., "Railing cells along 3D microelectrode tracks for continuous-flow dielectrophoretic sorting," Lab on a Chip, 2018, 18(24):3760-3769.

Lyu, C., et al., "Simultaneous electroporation and dielectrophoresis in non-electrolytic micro/nano-electroporation," Scientific Reports, 2018, 8:1-13.

Choi, Y.-S., et al., "Three Dimensional Electrode Structure Controlled by Dielectrophoresis for Flow-Through Micro Electroporation System," 19th IEEE International Conference on Micro Electro Mechanical Systems, 2006, pp. 1-2.

* cited by examiner

DEVICE FOR CELL TREATMENT

CROSS-REFERENCE TO RELATED APPLICATION

The subject application claims the benefit of U.S. Provisional Application Ser. No. 63/303,463, filed Jan. 26, 2022, which is incorporated herein by reference in its entirety.

BACKGROUND OF THE INVENTION

Intracellular delivery is the process of introducing exogenous agents, including proteins, nucleic acids, or small molecules such as drugs into cells for therapeutic applications (for example, drug delivery or gene editing) [1]. Electroporation is one of the popular nonviral intracellular delivery methods that enables the cellular intake of exogenous biomolecules by reversibly breaching cell membrane under a strong electric field [2]. In commercial bulk electroporation, high voltages with short pulses are applied through the cell suspension by a pair of electrodes and the electroporation occurs when the transmembrane potential exceeds the dielectric breakdown voltage and transient small pores form on the cell membrane. However, adverse effects on the treated cells often emerge due to excessive pulse strength which leads to irreversible membrane damage and low cell viability. Further, the cell treatment throughput of commercial electroporation operated in a batch mode is low and post-processing of the treated cells in a continuous operation is very difficult.

Continuous-flow microfluidic devices have been developed to achieve high-throughput cell electroporation and transfection for therapeutic applications such as cell reprogramming and gene silencing [3]. However, most existing platforms suffer from heterogeneous cell transfection since cells experience non-uniform electric field due to their random distributions in the microchannel. This issue could be addressed by bringing cells close to the electrodes under electrokinetic forces [4]. Previously, continuous-flow cell railing and sorting on three-dimensional (3D) microelectrode tracks under dielectrophoresis were demonstrated and cells were docked to microelectrodes under positive dielectrophoretic (pDEP) force [5].

Most microfluidic devices employ thin-film microelectrodes by metal deposition and patterning owing to the simple fabrication process. However, these microelectrodes extend exponentially attenuated electric fields at regions away from the microelectrodes, leading to low performance. Thin metal films are also prone to degradation and may cause electrolysis which is detrimental to bio-samples [6]. 3D microelectrodes are thereby introduced to solve these issues. Conventional 3D metal microelectrodes can create uniform electric fields but usually require complex fabrication processes such as SU-8 molding and electroplating. Further, they suffer from the same microelectrode degradation and electrolysis issues as thin-film metal microelectrodes [7]. Newly developed 3D microelectrodes use materials such as carbon [8] and polydimethylsiloxane (PDMS)-Ag powder composites [9] through simple fabrication processes and exhibit high biocompatibility. However, most of these microelectrodes are pillars and blocks in quasi-2D profile. Thus, they are limited in sidewall design variations and the ability to generate complex electric field distribution. 3D silicon microelectrodes, in comparison, exhibit various sidewall designs [10,11] as a result of tailored etching profile through a single mask. The designs also ease electro-fluidic integration.

BRIEF SUMMARY OF THE INVENTION

There continues to be a need in the art for improved designs and techniques for a method and apparatuses for high-throughput cell electroporation and transfection for therapeutic and other relevant applications.

According to an embodiment of the subject invention, a three-dimensional (3D) microelectrode array for flow-through microfluidic apparatuses is provided. The 3D microelectrode array comprises one or more microelectrode units formed with an interdigitated pattern. The one or more microelectrode units comprise microelectrode units in pairs. Each microelectrode unit of the one or more microelectrode units comprises a plurality of microelectrode pillars spaced apart from each other and a plurality of connecting microelectrode tracks disposed on top surfaces of the microelectrode pillars and interconnecting adjacent microelectrode pillars. Each microelectrode unit is formed in a shape of a viaduct having a plurality of micro-arches. Each micro-arch of the plurality of micro-arches has a shape of an oval. Moreover, widths of any one of the microelectrode tracks connecting two adjacent microelectrode pillars gradually decrease from centers of the adjacent microelectrode pillars to centers of spaces between the adjacent microelectrode pillars.

In certain embodiment of the subject invention, a method of making a 3D microelectrode array for flow-through microfluidic apparatuses is provided, comprising providing a silicon-on-insulator (SOI) wafer; sputtering a layer of aluminum onto the SOI wafer and patterning the layer of aluminum for electrical connections; depositing a layer of silicon dioxide ($SiO_2$) on top of the layer of aluminum; patterning the layer of $SiO_2$; forming silicon tracks by deep reactive ion etching (DRIE) through an oxide hard mask; depositing a layer of low-temperature oxide (LTO); selectively removing portions of the layer of LTO from a channel floor by anisotropic etching; forming sidewall undercuts for micro-arches by isotropic dry etching in $SF_6$ plasma to remove exposed silicon to expose buried oxide layer, isolate comb-like interdigitated microelectrodes, and create a flow chamber; and stripping off the deposited oxide layer by wet etching. The SOI wafer may have a thickness of 500 μm, comprising a device layer of a thickness of 75 μm and a buried oxide layer of a thickness of 2 μm. The layer of aluminum may have a thickness of 400 nm. The method of making a 3D microelectrode array may further comprise sealing the flow chamber after oxygen plasma surface activation by a polydimethylsiloxane (PDMS) slab with electrical and fluidic access holes. In addition, the method of making a 3D microelectrode array may further comprise connecting the 3D microelectrode array to external conductors by silver paste.

In some embodiments of the subject invention, a flow-through microfluidic apparatus for cell treatment comprises a flow chamber and the 3D microelectrode array described above disposed in the flow chamber to produce electrical fields for cell railing, electroporation and/or sorting. The flow chamber comprises a sample flow region, a first sheath flow region and a second sheath flow region. The sample flow region has a first input allowing a sample flow of a plurality of cells and one or more exogenous agents to enter the sample flow region, a first output allowing cells that are damaged to exit from the flow chamber, and a first fluid channel region having a first path defined therein between the first input and the first output and configured for the cells and the exogenous agents to flow. The first sheath flow region has a second input configured to allow a first sheath flow to enter the first sheath flow region, a second output configured to allow viable transfected cells to exit from the flow chamber, and a second fluid channel region having a second path defined therein between the second input and the second output and configured for the first sheath flow to flow. The second sheath flow region has a third input configured to allow a second sheath flow to enter the second sheath flow region and a third output to allow the second sheath flow to exit from the second sheath flow region. Moreover, the 3D microelectrode array is disposed to be inclined at a predetermined angle with respect to a flow direction of the flow chamber. The predetermined angle may be in a range between 0° and 90°, for example, between about 7° and about 26°. The first sheath flow and the second sheath flow each includes dielectrophoretic (DEP) buffer.

In some embodiments of the subject invention, a method of cell treatment comprises DEP railing of viable target cells along a plurality of 3D microelectrode units; electroporating of railing cells through electrical shocks to render the railing cells susceptible to intake/uptake of an exogenous agent; and DEP sorting of viable treated cells loaded with exogenous agent from cells damaged during the treatment. The DEP railing of viable target cells along the 3D microelectrode units comprises applying electric fields to the 3D microelectrode units such that the cells are docked against tracks of the 3D microelectrode units by DEP force towards maxima of the electric fields and rail along the tracks under the combined action of the DEP force and hydrodynamic drag; and dynamically tuning the DEP force in relation to the hydrodynamic drag by a modulated activation of the electric fields. The electroporating of railing cells comprises applying a predetermined pattern of bursts of electrical potential to the 3D microelectrode units. Burst counts, burst peaks, burst durations, or burst frequencies of the predetermined pattern of bursts of electrical potential are adjusted to maximize cell transfection rates. The predetermined pattern of bursts of electrical potential may comprise bursts of electrical potential having sinusoidal waveform or bursts of electrical potential having other suitable waveforms. Moreover, the electroporating of railing cells and the DEP sorting of viable treated cells loaded with exogenous agent from cells damaged are performed concurrently.

BRIEF DESCRIPTION OF THE DRAWINGS

FIG. 2A is a schematic diagram of simulated electric field distributions of the channel for an applied voltage pulse of 25 $V_p$ shown from top and cross-sectional views (I & II), wherein the spacing between comb-like electrodes is 150 μm, the chamber width and depth are 2.5 mm and 75 μm, respectively, and tracks extend at about 16° with respect to the flow direction, according to an embodiment of the subject invention.

FIGS. 5A-5D show experiment results of railing of HEK293 cells in 0.02 S/m buffer, wherein FIG. 5A shows cell railing efficiency as a function of activation frequency applied at 8 $V_p$; wherein FIG. 5B shows superimposed images demonstrating cells along tracks under 1 MHz activation with railing (red arrows) at 8 $V_p$ (above) and being trapped (red circles) at 15 $V_p$; wherein FIG. 5C shows cell railing efficiency and average velocity under a modulated activation at 1 MHz with 15 $V_p$ applied for 1 s followed by 8 $V_p$ for 0.5, 1 or 5 s; wherein FIG. 5D shows superimposed images of a single railing cell in relation to 1 MHz activation waveform (frequency not in scale) modulated at 8 $V_p$ for either 0.5 s (above) or 1 s (below) and 15 $V_p$ for 1 s (both); wherein the railing efficiency in FIG. 5A and FIG. 5C is defined as the percent ratio of railing cells to the total number of cells entering the microfluidic device, wherein the error bars is ±s.d. (n=10), according to an embodiment of the subject invention.

FIG. 6A shows bright field and fluorescence images of viable and transfected cells with Cascade Blue-tagged 3 kDa dextran (arrows), FIG. 6B shows confocal images from a viable transfected cell, FIG. 6C shows plot diagrams demonstrating cells viability and transfection rate in relation to peak voltage, FIG. 6D shows plot diagrams demonstrating cells viability and transfection rate in relation to burst durations, and FIG. 6E shows plot diagrams demonstrating cells viability and transfection rate in relation to burst-to-burst intervals, wherein modulated activation is 15 ms, bursts are applied at 100 kHz and 25 $V_p$, and with 2 s intervals, unless otherwise specified, wherein cell viability and cell transfection rate refer to the percent ratio of viable cells to total cells and the percent ratio of transfected cells to viable cells, respectively, wherein flow rate is 2 mL/hr, and wherein conductivity is 0.02 S/m, according to an embodiment of the subject invention.

FIG. 7A shows fluorescent images demonstrating the delivery of 3 kDa dextran into trapped HEK 293 cells after applying 5, 20 or 50 bursts of electrical potential with a magnitude of 25 $V_p$, and FIG. 7B shows plot diagrams demonstrating the cell transfection rate in relation to burst counts, burst peaks, burst durations and burst frequencies, wherein the individual burst has a duration of 25 ms, a frequency of 40 kHz, a magnitude of 25 $V_p$, and an interval of 2 s between successive bursts unless otherwise stated, and wherein DEP activation is 400 kHz, 10 $V_p$, according to an embodiment of the subject invention.

FIG. 8A shows fluorescent images of transfected cells (circled) railing into dextran-free sheath flow with no fluorescent background, when 5, 20 or 50 bursts at 40 kHz, 25 $V_p$ with an interval of 0.5 s between successive bursts are applied to electroporate cells in the sample flow containing 3 kDa dextran, wherein an underlying activation of 400 kHz, 10 $V_p$ is constantly applied for cell railing, sample flow is 0.5 mL/h, sheath flow is 0.3 mL/h; FIG. 8B shows fluorescent intensities of transfected cells demonstrating dextran intake in relation to the number of bursts applied to the railing cells, and FIG. 8C shows a superimposed image of a Hoechst 33342 stained HEK 293 cell demonstrating the counterclockwise rotating (rolling) behavior of a railing cell, wherein the image series show successive frames with an interval of 50 ms, according to an embodiment of the subject invention.

DETAILED DISCLOSURE OF THE INVENTION

The embodiments of subject invention pertain to a method and apparatuses for conducting DEP cell railing, electroporation and sorting in continuous flow for intracellular delivery.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention pertains. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

When the term "about" is used herein, in conjunction with a numerical value, it is understood that the value can be in a range of 90% of the value to 110% of the value, i.e. the value can be +/−10% of the stated value. For example, "about 1 kg" means from 0.90 kg to 1.1 kg.

Further, when the term "railing" is used herein, it is understood that "railing" is interpreted as "railing and/or rolling".

In describing the invention, it will be understood that a number of techniques and steps are disclosed. Each of these has individual benefits and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1A:
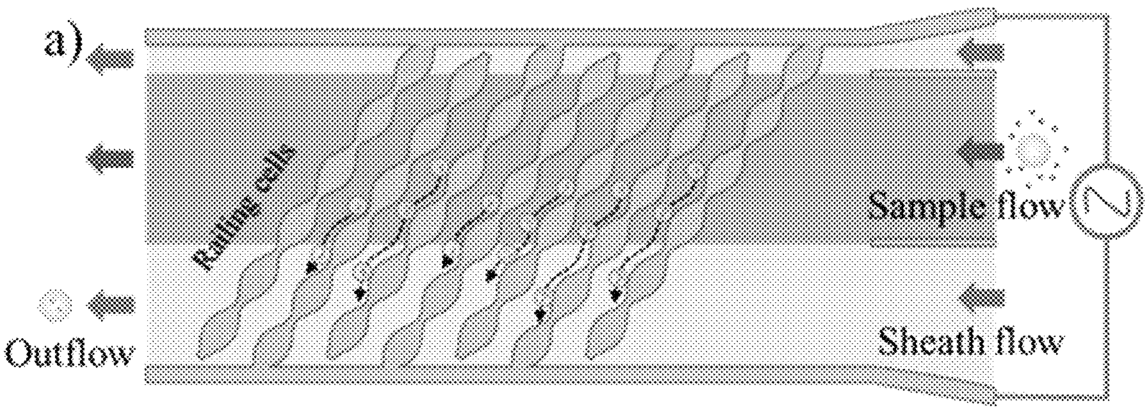
FIG. 1A is a schematic representation of the design layout of the flow-through microfluidic apparatus having a three-dimensional (3D) microelectrode array.

Referring to FIG. 1A, a flow-through microfluidic apparatus for cell treatment such as intracellular or cytosolic delivery of exogeneous agents is provided. The flow-through microfluidic apparatus comprises a flow chamber and a three-dimensional (3D) microelectrode array disposed in the flow chamber to produce electrical fields for cell railing, electroporation and/or sorting.

The flow chamber comprises a sample flow region, a first sheath flow region, and a second sheath flow region. The sample flow region has a first input allowing a sample flow of a plurality of cells and one or more exogenous agents to enter the sample flow region, a first output allowing cells that are damaged to exit from the flow chamber, and a first fluid channel region having a first path defined therein between the first input and the first output and configured for the cells and the exogenous agents to flow. The first sheath flow region has a second input configured to allow a first sheath flow to enter the first sheath flow region, a second output configured to allow viable transfected cells to exit from the flow chamber, and a second fluid channel region having a second path defined therein between the second input and the second output and configured for the first sheath flow to flow. The second sheath flow region has a third input configured to allow a second sheath flow to enter the second sheath flow region and a third output to allow the second sheath flow to exit from the second sheath flow region.

In one embodiment, the first sheath flow and the second sheath flow each includes DEP buffer.

As illustrated in FIG. 1A, the 3D microelectrode array is disposed to be inclined at a predetermined angle with respect to a flow direction of the flow chamber of the flow-through microfluidic apparatus.

Figure 1B:
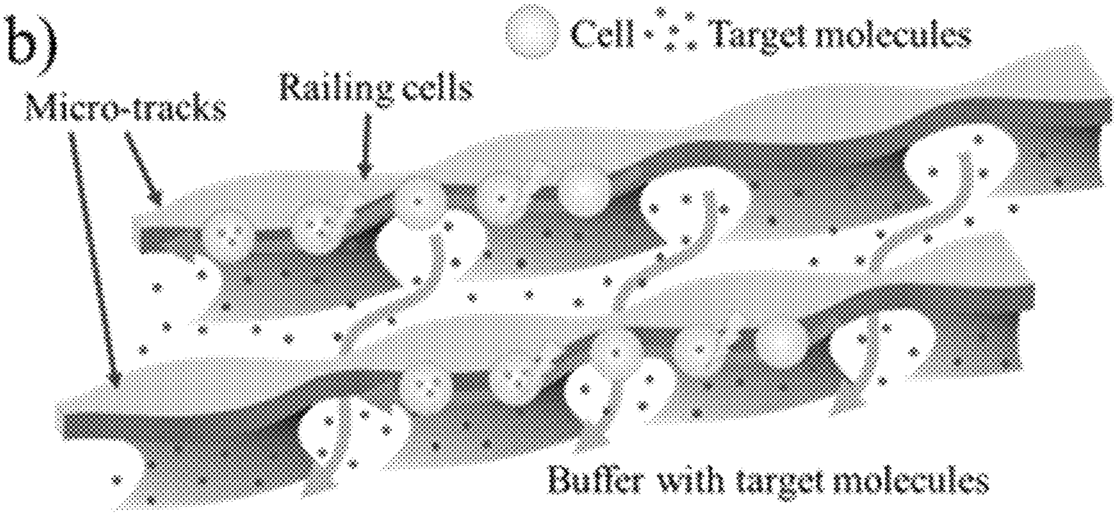
FIG. 1B is a schematic representation of 3D rendition of the 3D microelectrode array showing the working principle of DEP-assisted cell electroporation.

Referring to FIG. 1B, the 3D microelectrode array comprises one or more microelectrode units formed with an interdigitated pattern. Each microelectrode unit comprises a plurality of microelectrode pillars spaced apart from each other and a plurality of connecting microelectrode tracks along which cells rail disposed on top surfaces of the microelectrode pillars and interconnecting adjacent microelectrode pillars. Each microelectrode unit is formed in a shape of a viaduct or a comb having a plurality of micro-arches between adjacent microelectrode pillars which support microelectrode tracks. Moreover, widths of any one of the microelectrode tracks connecting two adjacent microelectrode pillars gradually decrease from centers of the adjacent microelectrode pillars to centers of spaces between the adjacent microelectrode pillars.

In one embodiment, the one or more microelectrode units comprise microelectrode units in pairs.

In one embodiment, each micro-arch of the plurality of micro-arches has a shape of an oval.

As illustrated in FIG. 1A, electroporated and viable cells continue to rail along the 3D microelectrode array to reach the designated side outlet for collection. Therefore, the viable cells with exogenous agent intake are sorted from nonviable and damaged cells during the electroporation and the subsequently collected cells exhibit excellent viability and effective intracellular delivery.

In contrast to the conventional technology, the embodiments of the subject invention adopt 3D microelectrode arrays, instead of thin-film microelectrodes for cell railing. Further, in the embodiments of the subject invention, the electroporation and the sorting of railing cells are concurrently performed in a single stage as opposed to being sequentially conducted by two cascade stages (a first cell electroporation stage followed by a sorting stage where viable treated cells are sorted out from the cells damaged during the treatment) in the conventional technology.

Figure 1C:
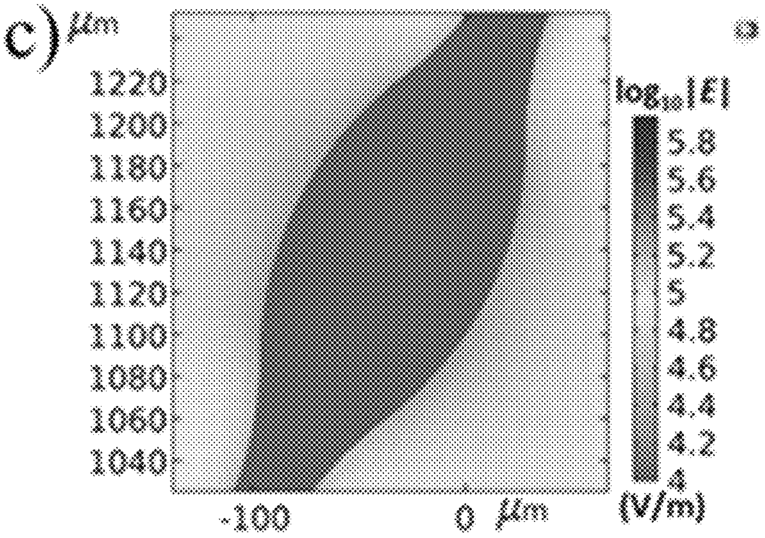
FIG. 1C shows simulation results of the electric field distributions near a single microelectrode unit of the 3D microelectrode array, according to an embodiment of the subject invention.

In the embodiments of the subject invention, cell railing is achieved by combined effect of DEP force and hydrodynamic drag. The 3D microelectrode array of the embodiments of the subject invention allows electric field maxima to form near the microelectrode tracks as shown in FIG. 1C. The electric field distribution in the microfluidic device, $E=-\nabla\phi$, can be derived from the Laplace Equation (1):

$$\nabla^2\phi = 0, \tag{1}$$

assuming homogeneous conductivity of the medium, with $\phi=V_0 \sin(2\pi f)$ being the applied potential, $V_0$ being the magnitude of activation voltage and f being frequency.

DEP refers to the motion of polarizable particles in an uneven electric field [12,13]. Assuming a cell has a spherical shape, the DEP force it undergoes can be expressed by Equation (2):

$$F_{DEP} = 2\pi\varepsilon_m r^3 \mathrm{Re}[K(\omega)]\nabla|E|^2 \tag{2}$$

with $\varepsilon_m$ being real permittivity of the extracellular medium and r being radius of the cell. Re[K(ω)] is the real part of the Clausius-Mossotti (CM) factor expressed by Equation (3):

$$K(\omega) = \frac{\tilde{\varepsilon}_i - \tilde{\varepsilon}_m}{\tilde{\varepsilon}_i + 2\tilde{\varepsilon}_m}, \tag{3}$$

in which ω is the angular frequency, while $\tilde{\varepsilon}_i$ and $\tilde{\varepsilon}_m$ refer to the complex permittivity of the cell and the medium, respectively, calculated from $\tilde{\varepsilon}_i=\varepsilon_i-j\sigma_i/\omega$ and $\tilde{\varepsilon}_m=\varepsilon_m-j\sigma_m/\omega$, respectively. $\varepsilon_i$ and $\varepsilon_m$ are the real permittivities, and $\sigma_i$ and $\sigma_m$ are the real conductivities of the intracellular and extracellular environments, respectively.

The sign of Re[K(ω)] determines the movement direction of cells in the electric field. Re[K(ω)]>0 or <0 indicates positive DEP (pDEP) or negative DEP (nDEP) and cells being attracted to or repelled from electric field maxima, correspondingly. Cells receive no DEP force at the crossover frequency $\omega_c$, where $\mathrm{Re}[K(\omega_c)]=0$.

According to the embodiments of the subject invention, cells are docked against the microelectrode tracks by the DEP force towards electric field maxima and rail along the microelectrode tracks under the combined action of the DEP force and hydrodynamic drag.

The imbalance of the DEP force and the hydrodynamic drag often leads to cell immobilization (excess DEP force and insufficient drag) or low railing efficiency (insufficient DEP force and excess drag). This problem can be addressed by a modulated activation of the electric fields to achieve efficient cell railing. When similar activation is also applied for continuous-flow cell electroporation, cell railing and cell transfection can be performed concurrently.

Herein, electroporation refers to cells undergoing treatment with short but intense electric bursts that create transient pores through their membrane for the intake of exogenous molecules [14]. The electric bursts can be adjusted to ensure reversible disruption and full recovery of the cell membrane.

The transmembrane potential under an oscillating electric field can be calculated by Schwan's equation (4) [15], assuming that the cell is spherical and its membrane is pure dielectric:

$$\Delta\psi_m = -1.5rE\cos\theta\left(1 - e^{-(t/\tau)}\right), \tag{4}$$

where θ is the polar angle between the local electric field direction and the normal vector from cell center to the point of calculation on the cell membrane, t is the time duration of the electric burst, and τ is the membrane relaxation time expressed by Equation (5):

$$\tau = rC_m/\left(\rho_i + \frac{\rho_m}{2}\right), \tag{5}$$

where $C_m$ represents membrane capacitance per unit area, and $\rho_i$ and $\rho_m$ are the resistivities of the cytoplasm and the extracellular medium, respectively.

In the embodiments of the subject invention, the microfluidic apparatus is provided for flow-through cell electroporation and DEP sorting treated cells that remain viable from cells damaged during treatment. In particular, viable target cells rail along the microelectrode tracks under the combined influence of DEP forces and hydrodynamic drag. Further electrical/mechanical treatment (electroporation/mechanoporation) can be applied to the railing cells via electrical pulses delivered by the microelectrodes and/or cells' physical contact with the microelectrodes. Next, an exogenous agent or agents are cytosolically delivered to the railing cells as a result of the electrical/mechanical treatment. Since damaged cells experience weaken DEP forces and unable to continue to rail along the microelectrodes, concurrent sorting of treated railing cells that remain viable from these railing cells being damaged during the treatment is achieved.

In one embodiment, the method can be applied to transfect mammalian cells with target exogenous agents, achieving high viablity and high transfection efficiency.

Figure 2A:
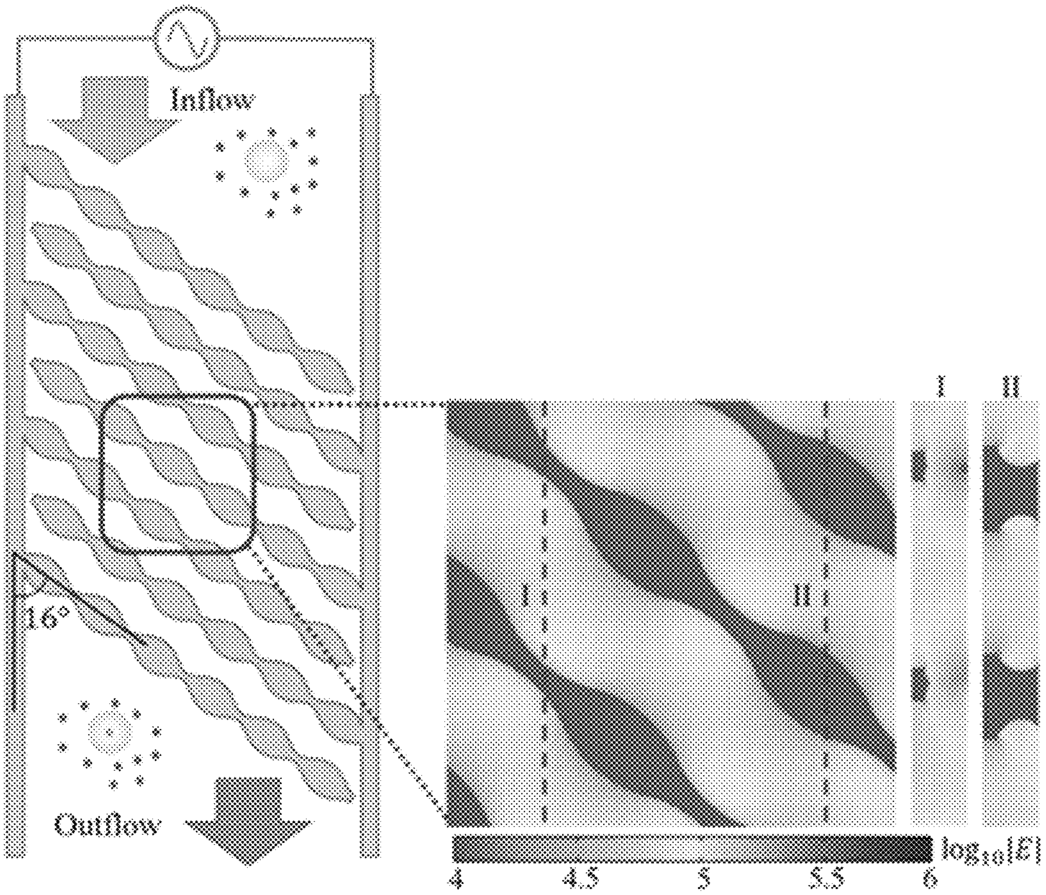
FIG. 2A is a schematic representation of layout of the microfluidic device.
Figure 2B:
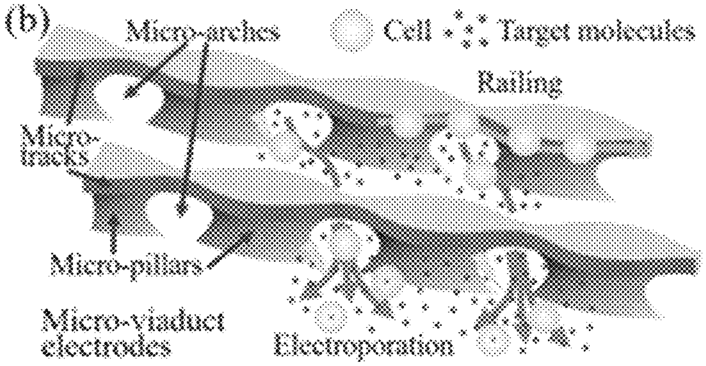
FIG. 2B is a schematic diagram of 3D rendition of the micro-viaduct microelectrodes with cells illustrated railing and being electroporated in the presence of target molecules.

Referring to FIG. 2A, in one embodiment of the subject invention, the flow-through microfluidic apparatus has the 3D microelectrode array disposed to be inclined at a predetermined angle in a range from about 7° to about 26° with respect to a flow direction of the flow chamber of the flow-through microfluidic apparatus. The spacing between the adjacent microelectrode units is about 150 μm and the flow chamber has a width of about 2.5 mm and a depth of about 75 μm. The computational results of the electric field distributions across the interdigitated microelectrodes for an applied voltage pulse of 25 $V_p$ are shown in FIG. 2A.

Fabrication of 3D Microelectrode Array

Figure 3:
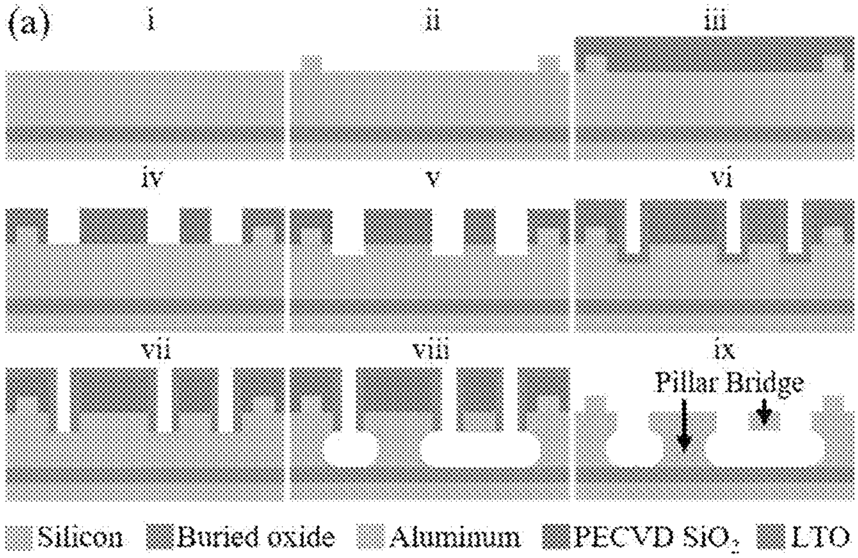
FIG. 3 is a schematic representation of the fabrication process of the three-dimensional (3D) microelectrode array including steps of: (i) starting SOI wafer, (ii) Al patterning, (iii) $SiO_2$ deposition, (iv) patterning, (v) Si DRIE, (vi) LTO deposition, (vii) floor oxide removal, (viii) isotropic etch, and (ix) oxide strip off, according to an embodiment of the subject invention.

As shown in FIG. 3(*i*), the 3D microelectrode array is fabricated based on a silicon-on-insulator (SOI) wafer which has a thickness of, for example, about 500 μm, comprising a device layer of a thickness of, for example, 75 μm and a buried oxide layer of a thickness of, for example, 2 μm. Then, a thin-film aluminum with a thickness of, for example, 400 nm is sputtered onto the SOI wafer and patterned for electrical connections, as shown in FIG. 3(*ii*). Next, a layer of silicon dioxide ($SiO_2$) is deposited on top of the layer of aluminum as shown in FIG. 3(*iii*). Then, the layer of $SiO_2$ is patterned as shown in FIG. 3(*iv*). Next, silicon tracks of a depth of, for example, 20 μm are formed by deep reactive ion etching (DRIE) through an oxide hard mask as shown in FIG. 3(*v*). Then, a layer of low-temperature oxide (LTO) is deposited as shown in FIG. 3(*vi*) and selectively removed from the channel floor by anisotropic etching as shown in FIG. 3(*vii*). Next, sidewall undercuts (micro-arches) are formed by isotropic dry etching in $SF_6$ plasma to remove the exposed silicon, expose the buried oxide layer, isolate the comb-like interdigitated microelectrodes, and create a flow chamber as shown in FIG. 3(*viii*). Then, the deposited oxide films are stripped off by wet etching as shown in FIG. 3(*ix*).

Further, the flow chamber may be sealed by an elastomer polydimethylsiloxane (PDMS) which may have a form of a slab with electrical and fluidic access holes after oxygen plasma surface activation. Subsequently, the microfluidic apparatus may be connected to copper wires by silver paste (for example, from Ted Pella, Inc., Redding, CA).

Figure 4:
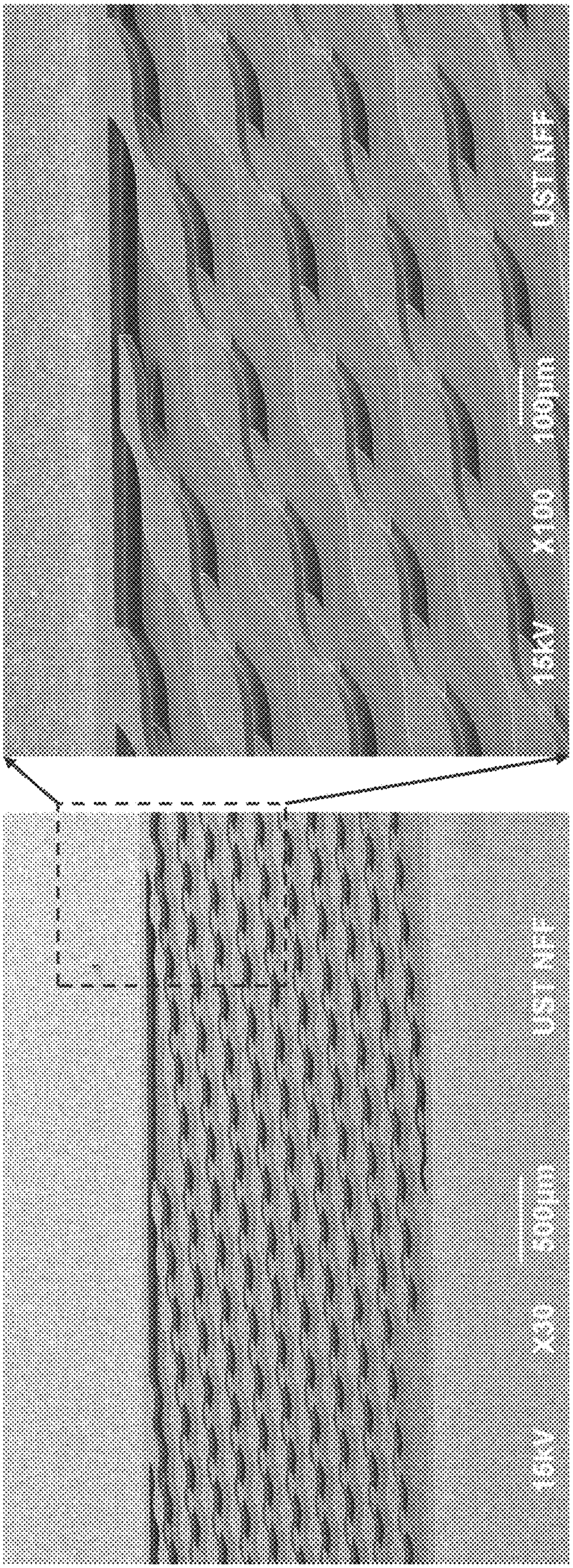
FIG. 4 shows SEM images of the fabricated 3D microelectrodes, according to an embodiment of the subject invention.

FIG. 4 shows SEM images of the fabricated 3D microelectrode array.

According to the embodiments of the subject invention, a method of cell treatment based on the flow-through microfluidic apparatus having the 3D microelectrode array is provided, comprising steps of DEP railing of viable target cells along a plurality of 3D microelectrode units; electroporating of railing cells through electrical pulses to render the railing cells susceptible to intake/uptake of an exogenous agent; and DEP sorting of viable treated cells loaded with exogenous agent from cells damaged during the treatment. Treated cells that suffer from irreversible membrane damage experience weakened pDEP force and are released from the railing microelectrode tracks and transported to the main outlet for discarding.

Cells rail along the 3D microelectrodes under the combined influence of pDEP force and hydrodynamic drag for simultaneous cell sorting to harvest viable and electroporated cells. Cell suspension containing an exogenous agent to be delivered into cells are injected into the flow chamber having the microelectrodes, which are configured to generate electric fields to dock cells onto the microelectrodes under the DEP force and electroporate cells under electroporation activation(s) by direct-current and/or alternating-current voltage pulses. The cells docked on the microelectrodes rail along the microelectrodes under the combined influence of pDEP force and hydrodynamic drag, and the railing cells losing viability during electroporation receive weakened DEP force, thereby being released from the microelectrodes. The microelectrodes are configured to guide viable and electroporated cells to the collection port, thereby realizing simultaneous cell electroporation and sorting. As a result, highly efficient and uniform electroporation can be realized, facilitating continuous-flow cell transfection.

Experiment Setup

Human embryonic kidney cells (for example, HEK 293) are cultured inside an incubator aerated with 5% $CO_2$. The culture medium comprises Dulbecco's Modified Eagle Medium (DMEM), 10% fetal bovine serum (FBS), and 1% penicillin/streptomycin (P/S).

Cells are detached from culture dishes with 0.05% trypsin/EDTA, and then pelleted with centrifugation at 800 rpm for 5 minutes, before being resuspended in fresh DMEM to a density of $10^5$ cells/mL. Cells are stained with calcein-AM dye (Invitrogen, Carlsbad, CA) in the dark for 15 minutes, and washed twice before being resuspended in phosphate-buffered saline (PBS) buffer with conductivity adjusted to 0.02 S/m by DI water and 300 mM D-mannitol (Sigma, St. Louis, MO). For electroporation experiments, the cell suspension is spiked with the target delivery molecule 3 kDa cascade blue-tagged dextran (for example, 0.3 mg/mL, Invitrogen, Carlsbad, CA).

The channel sidewalls are blocked against adhesion of cells with 5% bovine serum albumin. Cells are injected via a syringe pump (Harvard Apparatus, Holliston, MA) and observed under an epifluorescence microscope (Nikon Eclipse, FN1; Nikon, Tokyo, Japan) equipped with an EMCCD camera (iXon3, Andor Technology Ltd, UK). The modulated activation is delivered by a function generator (DG1022, Rigol Technologies Inc., Beijing, China) and then processed through an amplifier-transformer pair (AL-50TFA, Amp-Line Crop., West Nyack, NY). The activation is monitored by an oscilloscope (TDS-1072B-EDU, Tektronix, Beaverton, CA). For electroporation, cells are collected from the microfluidic device outlet, washed several times before being resuspended in DMEM. Further, the cells are observed on a microscope slide about minutes after collection and the number of total viable and dextran-transfected cells are counted for further analysis.

Cell Railing

Figure 5A:
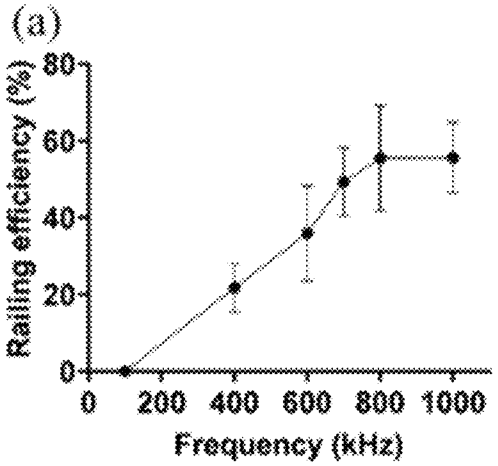
Figure 5B:
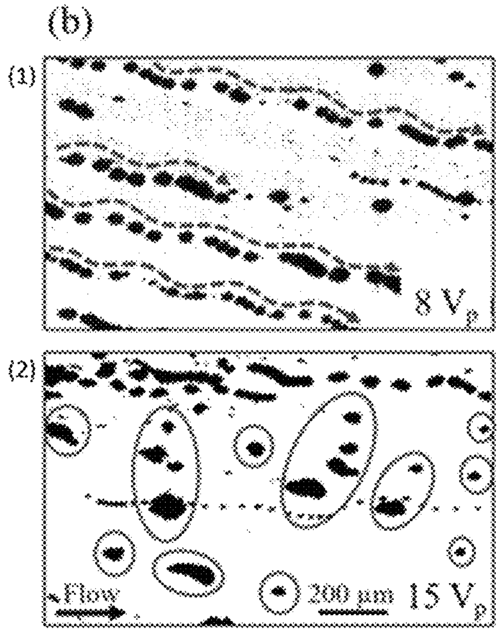
Figure 5C:
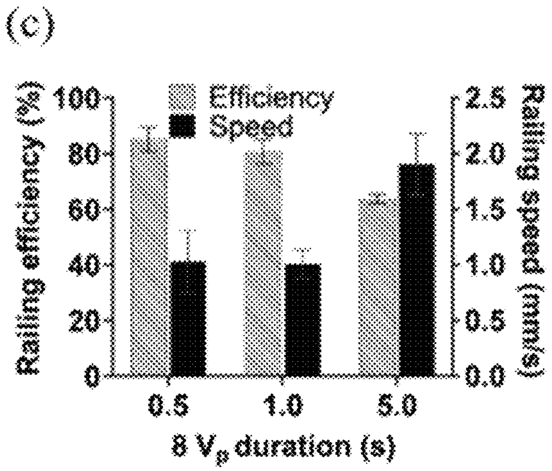
Figure 5D:
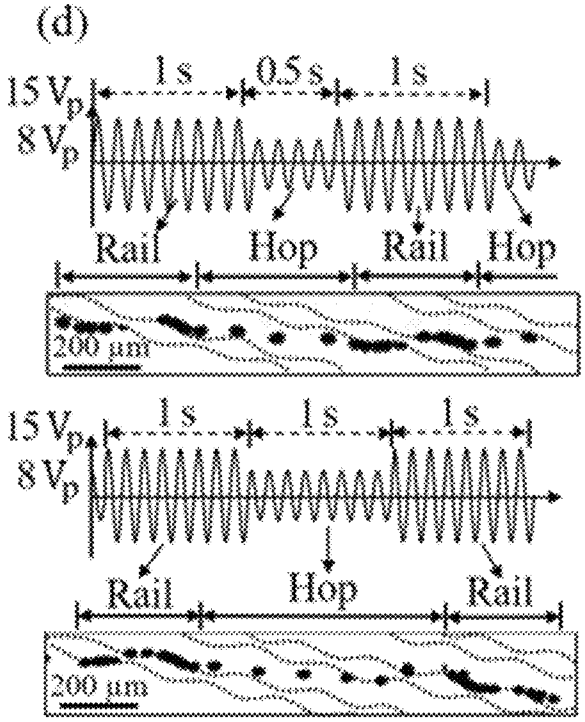

FIG. 5A shows the cell railing efficiency at 8 $V_p$ under sinewave activation with varying frequencies. At 100 kHz activation, no cell is seen railing due to insufficient pDEP force. When the activation frequency is increased, pDEP force is strengthened, leading to attraction of cells to the 3D microelectrodes and improvement of the railing efficiency. Yet, railing efficiency reaches a plateau at 800 kHz. At 1 MHz, only around 60% of cells are observed railing as shown in FIG. 5B(1). Raising activation voltage increases the pDEP force and results in an increased number of cells becoming docked onto the microelectrode tracks. However, cell railing is hindered because strong pDEP force immobilizes cells on the electrodes as shown by FIG. 5B(2). This issue is addressed through a modulated activation whereby 1 MHz activation is first applied at an amplitude of 15 $V_p$ for a period of 1 second and then at an amplitude of 8 $V_p$ for periods of 0.5 second, 1 second or 5 seconds, as shown in FIG. 5C. When 8 $V_p$ is applied for a period of 0.5 second or 1 second, around 80% of cells are seen railing, at an average speed of about 1 mm/s. When applied for 5 seconds, the railing efficiency drops to approximately 60%, while the average railing speed approaches to 2 mm/s. FIG. 5D shows the correlation between the modulated activation and the cell railing behavior. The cells are docked onto the microelectrode tracks during 15 $V_p$ activation. Although these cells begin to rail, railing decelerates due to hydrodynamic drag overtaken by pDEP force. Before the cells are completely immobilized, they become released from the microelectrode tracks in the subsequent activation cycle of 8 $V_p$ only to be recaptured again under the following 15 $V_p$ activation cycle. Thus, the cells flowing across the flow chamber by hopping from one electrode to the next. Such modulation allows the cells to travel through the 3D microelectrodes at an appreciable average velocity, improving railing throughput.

Dynamic tuning of the pDEP force in relation to hydrodynamic drag exerted on cells allows cells to effectively rail on the microelectrode tracks of the microelectrodes at a large track angle. A large track angle shortens the track length required for cells to cross the chamber, allowing for minimizing the size of the microfluidic apparatus. Moreover, it enhances the normal component of the fluidic drag while reducing the drag tangential component. This has conflicting requirements on the activation voltage; an increased voltage in the former to avoid cell escape and a reduced voltage in the latter to avoid cell immobilization. Modulated activation addresses this problem by allowing these cells to be periodically released and then recaptured by the microelectrodes downstream for them to continue to rail.

Cell Electroporation

Figure 6A:
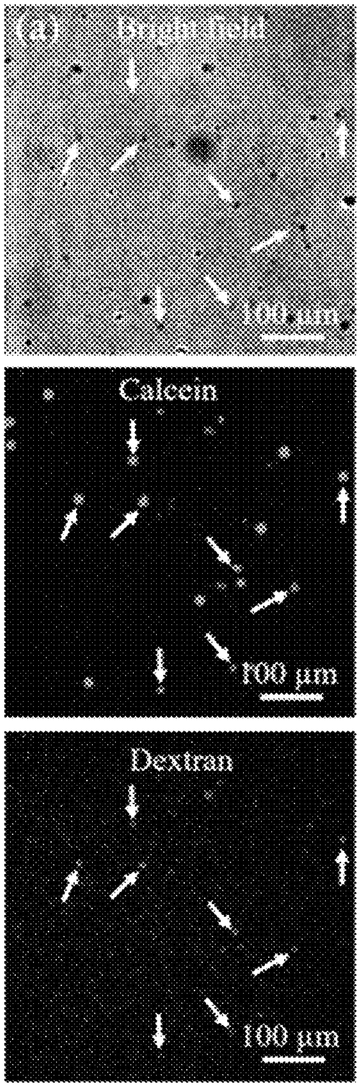
FIGS. 6A-6E show the results pertaining to cells being electroporated while traveling through the flow chamber without railing along the microelectrode tracks.
Figure 6B:
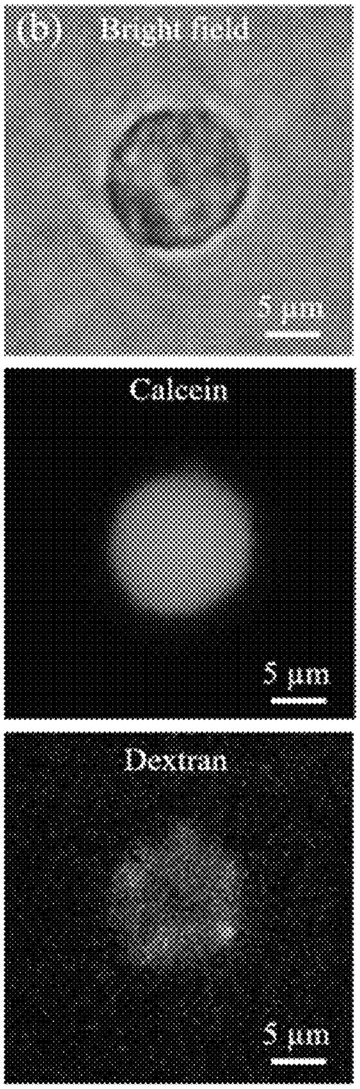

Modulated activation also plays a key role in the flow-through cell electroporation. Flow-through electroporation refers to the electroporation of cells freely flowing through the flow chamber without railing along the microelectrode tracks. Electrical activation is only applied to porate cells; no activation is applied for docking and railing cells along the microelectrode tracks, i.e., no pDEP. The modulated activation of 100 kHz bursts may be applied at 25 $V_p$, for 15 ms and 2 s intervals. Bright field and fluorescent images of cells harvested from the microfluidic device confirm that cells are successfully transfected with 3 kDa dextran and remain viable in FIG. 6A. In FIG. 6B, the confocal images of a representative cell exhibit an even distribution of dextran inside the cell instead of a localized cytosolic staining, indicating that the intake is resulted from electroporation, not from endocytosis.

Figure 6C:
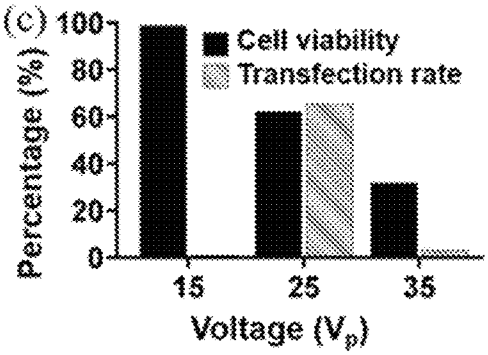
Figure 6D:
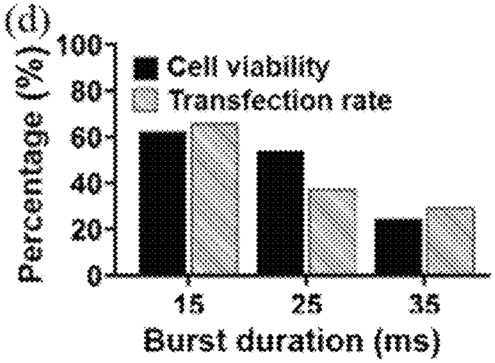
Figure 6E:
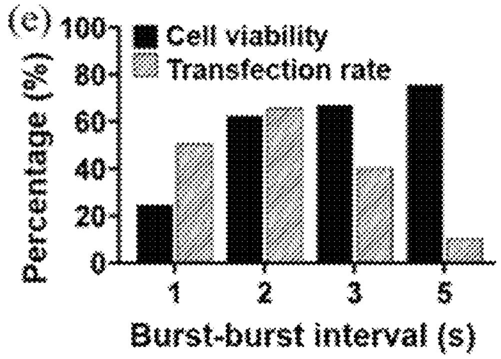

The influences of activation peak voltage on cell viability and transfection rate are demonstrated in FIG. 6C. Reducing the peak voltage to 15 $V_p$ results in high viability but almost no noticeable transfection, whereas increasing the peak voltage to 35 $V_p$ causes cell viability to plunge. An activation of 25 $V_p$ leads to effective electroporation while keeping more than half of the cell population viable. Increasing burst duration to 25 ms and 35 ms lowers both cell viability and transfection rate, while 15 ms bursts result in acceptable viability and transfection rate as shown in FIG. 6D. Further, it is revealed in FIG. 6E that a burst interval of 2 seconds results in a maximal transfection without a seriously compromised cell viability. The results indicate that modulated activation of 100 kHz bursts at 25 $V_p$ amplitude, 15 ms duration and the interval of 2 seconds yield the best transfection rate higher than 60%.

Figure 7A:
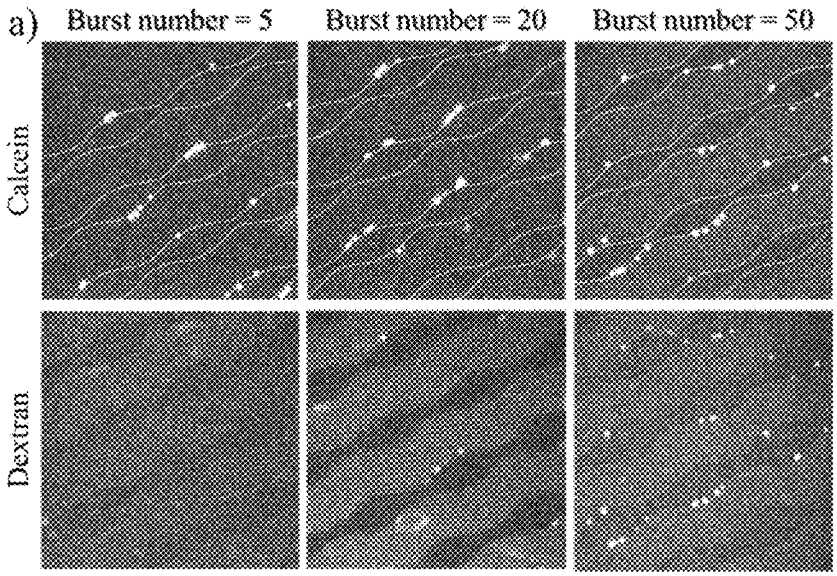
FIGS. 7A-7B show the results pertaining to cells being electroporated while immobilized on the microelectrode tracks without railing by pDEP force and under stagnant flow condition.
Figure 7B:
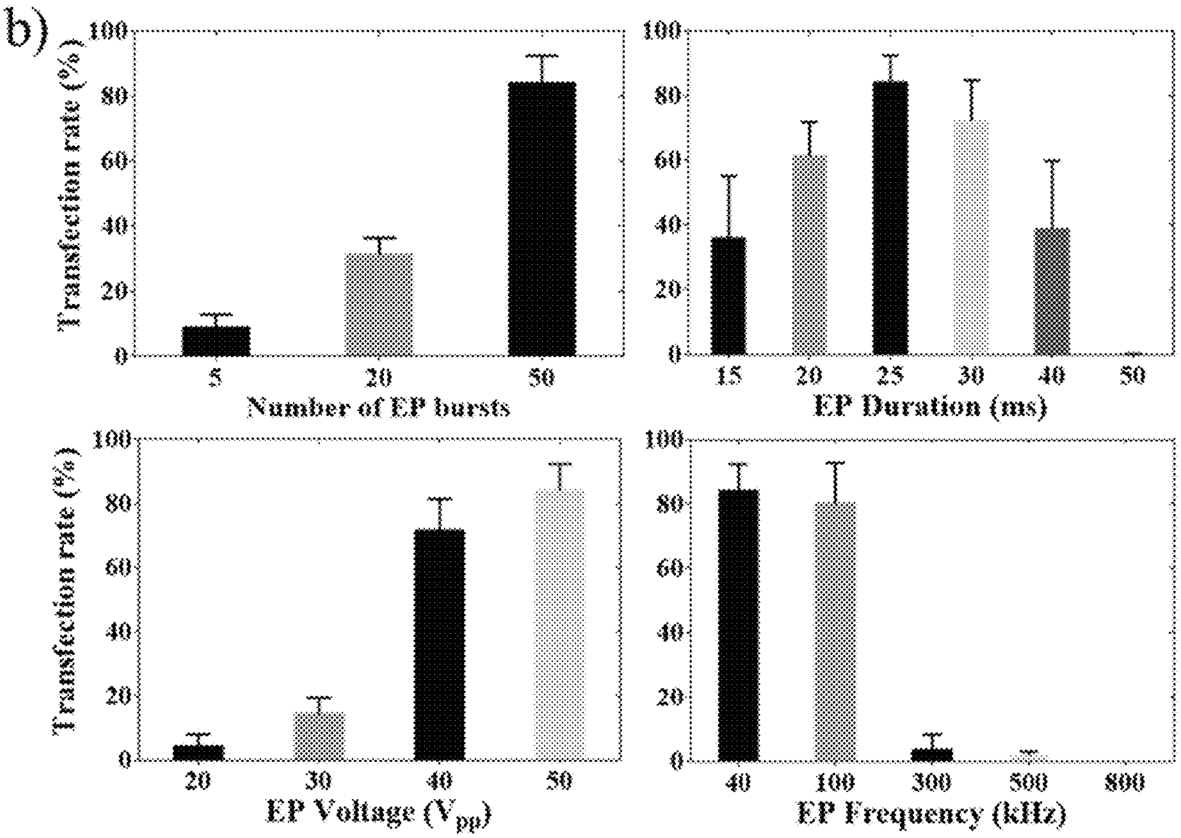
Figure 8A:
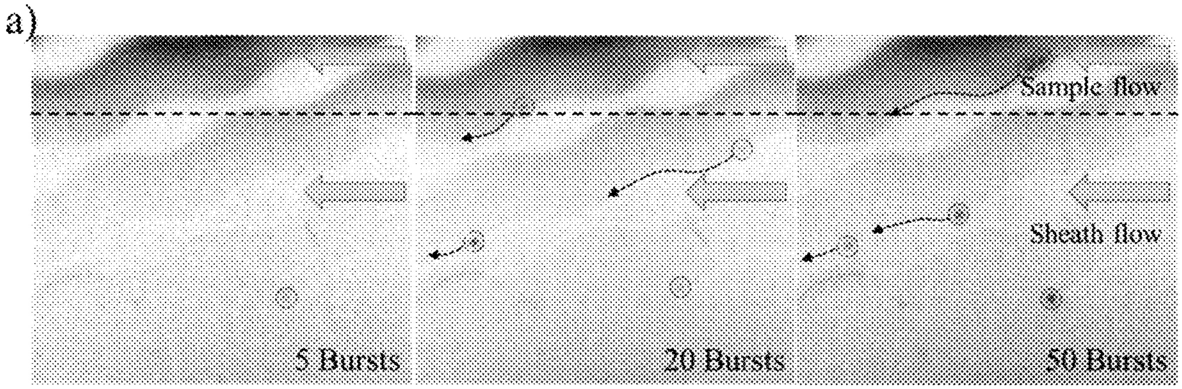
FIGS. 8A-8C show the results pertaining to cells being electroporated while railing along the microelectrode tracks under the combined action of the DEP force and hydrodynamic drag.
Figure 8B:
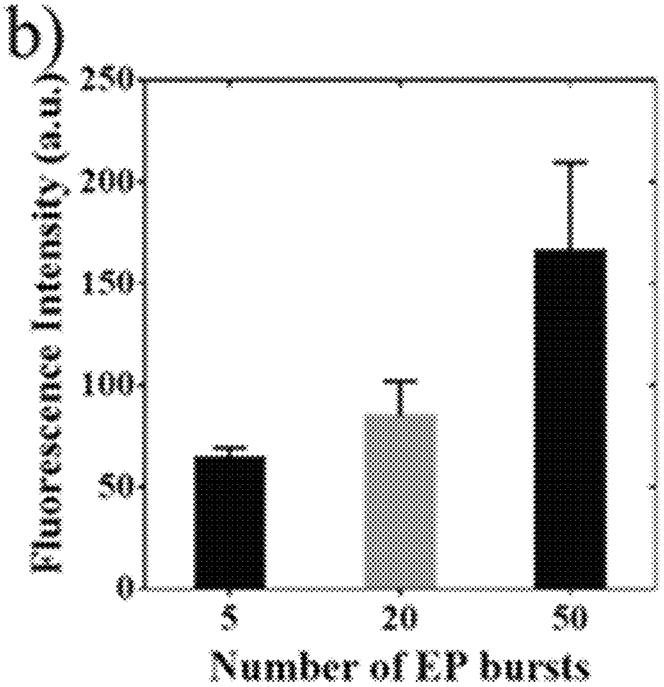
Figure 8C:
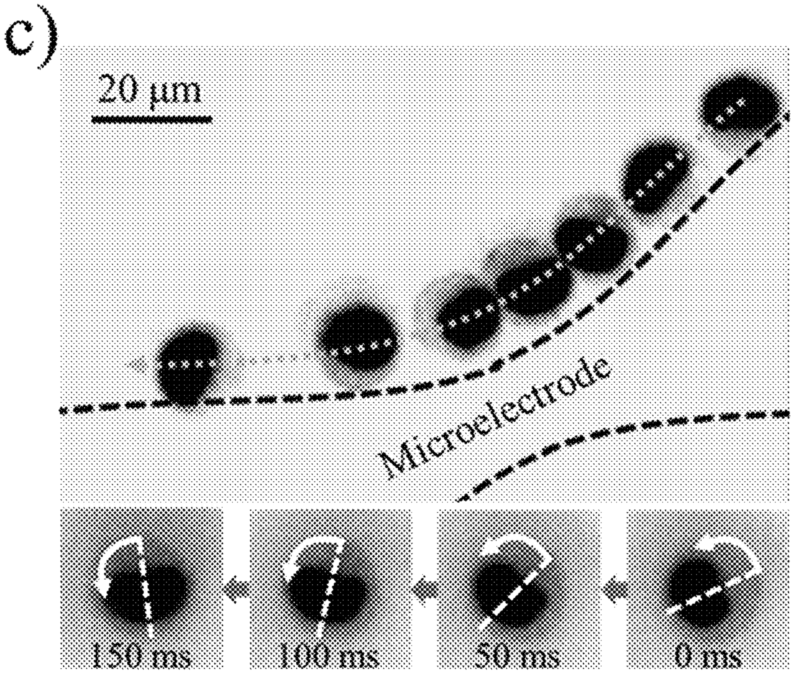

In one embodiment, electrical bursts such as bursts of electrical potential having sinusoidal waveform are applied to the cells immobilized on the 3D microelectrodes by the pDEP force under stagnant flow. That is, cells captured on microelectrodes do not rail due to the absence of hydrodynamic drag. This is to determine the optimal activation that can be applied to railing cells. Human embryonic kidney cells (HEK 293) are stained with calcein-AM dye and resuspended in DEP buffer (for example, PBS, conductivity: 0.02 S/m) containing cascade-blue tagged 3 kDa dextran and 300 mM D-mannitol. Cells are injected into the microfluidic device and docked to the microelectrodes under pDEP force activated at 400 kHz, 10 $V_p$. Meanwhile, bursts of electrical potential having sinusoidal waveform are applied for cell electroporation. FIG. 7A shows that the treated cells are positive in both calcein and dextran, indicating successful dextran delivery while maintaining cell viability. The transfection rate increases with the number of bursts of electrical potential applied, reaching approximately 85% under an optimal electroporation activation having 50 successive bursts of electrical potential having sinusoidal waveform at 40 kHz, 25 $V_p$ with a duration of 25 ms each as shown in FIG. 7B. A combination of cell railing and electroporation can improve transfection efficiency by attracting cells to the electric field maxima under pDEP. Simultaneously sorting and transfecting cells by railing can also be attained by superimposing short bursts on the modulated activation prescribed here for effective railing. The railing cells are electroporated in the main sample flow containing dextran molecules. Once cells rail along the microelectrode tracks into the sheath flow (for example, dextran-free buffer), the dextran-positive transfected cells can be clearly observed as in FIG. 8A. Increasing the number of bursts of electrical potential leads to a larger amount of dextran intake as shown in FIG. 8B. While railing, cells are observed to rotate counterclockwise (roll) as shown in FIG. 8C. The rotating or rolling behavior exposes different areas of cell membrane to the local electric fields, allowing uniform delivery of exogenous agents for continuous-flow cell transfection.

The multifunctional 3D microelectrodes are configured for cell railing, which is a prerequisite step for sorting cells. The railing efficiency is enhanced by dynamically tuning the DEP force in relation to the hydrodynamic drag exerted on cells through a modulated activation. The utility of 3D microelectrodes for continuous-flow cell electroporation and transfection is demonstrated. Moreover, simultaneously sorting and transfecting cells with exogenous agents such as DNA or plasmids for gene therapy can be achieved.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] Stewart, Martin P., et al. "In vitro and ex vivo strategies for intracellular delivery." *Nature* (2016): 183-192.

[2] Edd, Jon F., et al. "In vivo results of a new focal tissue ablation technique: irreversible electroporation." *IEEE Transactions on Biomedical Engineering* (2006): 1409-1415.; Tsong, Tian Yow. "Electroporation of cell membranes." *Electroporation and electrofusion in cell biology* (1989): 149-163.

[3] Kim, Jungkyu, et al. "Microfluidic approaches for gene delivery and gene therapy." *Lab on a Chip* (2011): 3941-3948.

[4] Xu, Youchun, et al. "The construction of an individually addressable cell array for selective patterning and electroporation." *Lab on a Chip* (2011): 2417-2423.

[5] Xing, Xiaoxing, et al. "Railing cells along 3D microelectrode tracks for continuous-flow dielectrophoretic sorting." *Lab on a Chip* (2018): 3760-3769.

[6] Geng, Tao, and Chang Lu. "Microfluidic electroporation for cellular analysis and delivery." *Lab on a Chip* (2013): 3803-3821.

[7] Martinez-Duarte, Rodrigo. "Microfabrication technologies in dielectrophoresis applications—A review." *Electrophoresis* (2012): 3110-3132.

[8] Yildizhan, Yagmur, et al. "Dielectrophoretic separation of live and dead monocytes using 3D carbon-electrodes." *Sensors* (2017): 2691.

[9] Zhang, Zhongle, et al. "A one-step molded microfluidic chip featuring a two-layer silver-PDMS microelectrode for dielectrophoretic cell separation." *Analyst* (2020): 5603-5614.

[10] Xing, Xiaoxing, et al. "Continuous-flow electrokinetic-assisted plasmapheresis by using three-dimensional microelectrodes featuring sidewall undercuts." *Analytical chemistry* (2016):5197-5204.
[11] Xing, Xiaoxing, et al. "Railing cells along 3D microelectrode tracks for continuous-flow dielectrophoretic sorting." *Lab on a Chip* (2018): 3760-3769.
[12] Castellanos, Antonio, et al. "Electrohydrodynamics and dielectrophoresis in microsystems: scaling laws." *Journal of Physics D: Applied Physics* (2003): 2584.
[13] Morgan, Hywel, Michael P. Hughes, and Nicolas G. Green. "Separation of submicron bioparticles by dielectrophoresis." *Biophysical journal* (1999): 516-525.
[14] Kotnik, Tadej, et al. "Cell membrane electroporation—Part 1: The phenomenon." *IEEE Electrical Insulation Magazine* (2012): 14-23.
[15] Schwan, Herman P. "Electrical properties of tissue and cell suspensions." *Advances in biological and medical physics* (1957): 147-209.

We claim:

1. A flow-through microfluidic apparatus for cell treatment, comprising:

a flow chamber; and a three-dimensional (3D) microelectrode array disposed in the flow chamber and configured to produce electrical fields for cell railing, electroporation, and sorting;

wherein the flow chamber comprises a sample flow region, a first sheath flow region, and a second sheath flow region;

wherein the sample flow region has a first input allowing a sample flow of a plurality of cells and one or more exogenous agents to enter the sample flow region, a first output allowing cells that are damaged to exit from the flow chamber, and a first fluid channel region having a first path defined therein between the first input and the first output and configured for the cells and the exogenous agents to flow;

wherein the first sheath flow region has a second input configured to allow a first sheath flow to enter the first sheath flow region, a second output configured to allow viable transfected cells to exit from the flow chamber, and a second fluid channel region having a second path defined therein between the second input and the second output and configured for the first sheath flow to flow;

wherein the second sheath flow region has a third input configured to allow a second sheath flow to enter the second sheath flow region and a third output to allow the second sheath flow to exit from the second sheath flow region, and wherein the same 3D microelectrode array that rails the cells is further configured to apply electroporation pulses to the railing cells and to concurrently dielectrophoretically sort viable electroporated cells from damaged cells, such that damaged cells experience a weakened dielectrophoretic (DEP) force and are released from microelectrode tracks.

2. The flow-through microfluidic apparatus of claim 1, wherein the 3D microelectrode array is disposed to be inclined at a predetermined angle with respect to a flow direction of the flow chamber.

3. The flow-through microfluidic apparatus of claim 2, wherein the predetermined angle is in a range between about 0° and about 90°.

4. The flow-through microfluidic apparatus of claim 3, wherein the predetermined angle is in a range between about 7° and about 26°.

5. The flow-through microfluidic apparatus of claim 1, wherein the first sheath flow and the second sheath flow each includes dielectrophoretic buffer.

6. The flow-through microfluidic apparatus of claim 1, wherein the three-dimensional (3D) microelectrode array comprises a microelectrode unit comprising a microelectrode pillar and a microelectrode track disposed on a top surface of the microelectrode pillar.

7. The flow-through microfluidic apparatus of claim 6, wherein a space of a rectangular or oval shape is formed between the microelectrode pillar and an adjacent portion of the microelectrode track.

8. The flow-through microfluidic apparatus of claim 1, wherein the three-dimensional (3D) microelectrode array comprises one or more microelectrode units formed with an interdigitated pattern, each microelectrode unit being formed in a shape of a viaduct having a plurality of micro-arches.

9. The flow-through microfluidic apparatus of claim 8, wherein each micro-arch of the plurality of micro-arches has a shape of an oval.

10. The flow-through microfluidic apparatus of claim 8, wherein each microelectrode unit of the one or more microelectrode units comprises a plurality of microelectrode pillars spaced apart from each other and a plurality of connecting microelectrode tracks disposed on top surfaces of the microelectrode pillars and interconnecting adjacent microelectrode pillars.

11. The flow-through microfluidic apparatus of claim 10, wherein a width of any one of the microelectrode tracks connecting two adjacent microelectrode pillars gradually decreases from centers of the adjacent microelectrode pillars to centers of spaces between the adjacent microelectrode pillars.

12. The flow-through microfluidic apparatus of claim 8, wherein the one or more microelectrode units comprise microelectrode units in pairs.

13. The flow-through microfluidic apparatus of claim 1, wherein the 3D microelectrode array is made of single crystal silicon.

14. The flow-through microfluidic apparatus of claim 1, wherein the 3D microelectrode array is made of single crystal silicon by tailoring dry etch profile.

15. The flow-through microfluidic apparatus of claim 1, wherein the 3D microelectrode array is built into a device layer of a silicon-on-insulator substrate.

16. The flow-through microfluidic apparatus of claim 1, wherein the 3D microelectrode array is built into a thin silicon wafer bonded over an insulating substrate.

* * * * *